(12) United States Patent  (10) Patent No.: US 8,750,591 B2
Pfister  (45) Date of Patent: Jun. 10, 2014

(54) ANGIOGRAPHY SYSTEM FOR ANGIOGRAPHIC EXAMINATION OF AN OBJECT UNDER EXAMINATION AND ANGIOGRAPHIC EXAMINATION METHOD

(75) Inventor: Marcus Pfister, Bubenreuth (DE)

(73) Assignee: Siemens Aktiengesellschaft, München (DE)

( * ) Notice: Subject to any disclaimer, the term of this patent is extended or adjusted under 35 U.S.C. 154(b) by 91 days.

(21) Appl. No.: 13/433,400

(22) Filed: Mar. 29, 2012

(65) Prior Publication Data
US 2012/0250964 A1  Oct. 4, 2012

(30) Foreign Application Priority Data

Mar. 31, 2011 (DE) .................. 10 2011 006 484

(51) Int. Cl.
G06K 9/00 (2006.01)
A61B 6/03 (2006.01)
(52) U.S. Cl.
USPC ............................................ 382/131; 378/17
(58) Field of Classification Search
None
See application file for complete search history.

(56) References Cited

U.S. PATENT DOCUMENTS

| 7,500,784 | B2 | 3/2009 | Grebner |
| 7,734,009 | B2 | 6/2010 | Brunner |
| 2007/0021668 | A1 | 1/2007 | Boese et al. |
| 2007/0265551 | A1 | 11/2007 | Pfister |
| 2010/0014629 | A1 | 1/2010 | Boese |
| 2010/0014740 | A1* | 1/2010 | Movassaghi et al. ......... 382/132 |
| 2011/0052026 | A1* | 3/2011 | Liao et al. .................... 382/131 |

FOREIGN PATENT DOCUMENTS

| DE | 102005032523 A1 | 1/2007 |
| DE | 102006020402 B3 | 11/2007 |
| DE | 102008033137 A1 | 2/2010 |

OTHER PUBLICATIONS

Product Guide: Guidewires Stent Grafts by Medtronic and Lombard Medical Technologies Cardiology today, Jan. 2011, p. 36,; Others.

* cited by examiner

Primary Examiner — Jon Chang

(57) ABSTRACT

An angiography system for angiographic examination or treatment of an organ, vascular system or other regions of an object of a patient is proposed. The system has an x-ray source and an x-ray image detector disposed at ends of a C-arm, a patient support table, a system control unit, an image system, and a monitor. The object contains two details hiding each other in the x-ray images depending on angulation of the C-arm. The system control unit has a device that detects a 3D dataset of the object registered to the C-arm and detects the information about a course of the object. The device calculates a desired and/or optimum angulation of the C-arm from the detected information and transfers the calculated angulation to the system control unit for adjusting the C-arm to the angulation.

13 Claims, 5 Drawing Sheets

ANGIOGRAPHY SYSTEM FOR ANGIOGRAPHIC EXAMINATION OF AN OBJECT UNDER EXAMINATION AND ANGIOGRAPHIC EXAMINATION METHOD

CROSS REFERENCE TO RELATED APPLICATIONS

This application claims priority of German application No. 10 2011 006 484.2 filed Mar. 31, 2011, which is incorporated by reference herein in its entirety.

FIELD OF INVENTION

The invention relates to an angiography system for angiographic examination or treatment of an organ, vascular system or other regions of the body of a patient as the object under examination.

BACKGROUND OF INVENTION

An angiography system of this type is known for example from U.S. Pat. No. 7,500,784 B2, and said system is explained below with reference to FIG. 1.

FIG. 1 shows a monoplane x-ray system presented by way of example with a C-arm 2 in the form of a six-axis industrial or articulated-arm robot supported by a stand 1, to the ends of which an x-radiation source, for example an x-ray emitter 3 with x-ray tube and collimator and an x-ray image detector 4 as an image recording unit are attached.

By means of the articulated-arm robot known from the above-mentioned U.S. Pat. No. 7,500,784 B2, which preferably has six axes of rotation and thereby six degrees of freedom, the C-arm 2 can be adjusted spatially in any given manner by being rotated for example around a center of rotation between the x-ray emitter 3 and the x-ray image detector 4. The inventive angiographic x-ray system 1 to 4 is especially able to be rotated around centers of rotation and axes of rotation in the C-arm plane of the X-ray image detector 4, preferably around the central point of the x-ray image detector 4 and around axes of rotation intersecting the central point of the x-ray image detector 4.

The known articulated arm robot has a base frame which is solidly mounted on a floor for example. Attached thereto is the carousel able to be rotated around a first axis of rotation. Attached to the carousel is a robot stand able to be pivoted around a second axis of rotation to which a robot aim able to be rotated around a third axis of rotation is attached. Attached to the end of the robot arm is a robot hand able to be rotated around the fourth axis of rotation. The robot hand has an attachment element for the C-arm 2, which is able to be pivoted around a fifth axis of rotation and is able to be rotated around a sixth axis of rotation running at right angles thereto.

The x-ray diagnosis device does not rely on industrial robots. Normal C-arm devices can also be used.

The x-ray image detector 4 can be a rectangular or square flat semiconductor detector which is preferably made of amorphous silicon (a-Si). However integrating and if necessary counting CMOS detectors can also be used.

Located in the beam path of the x-ray emitter 3 on a table plate 5 of a patient support table is a patient 6 to be examined as the object under examination. Connected to the x-ray diagnosis device is a system control unit 7 with an image system 8 which receives and processes the image signals of the x-ray image detector 4 (control elements are typically not shown). The x-ray images can then be viewed on displays of a monitor array 9.

Instead of the x-ray system presented by way of example in FIG. 1 with the stand 1 in the form of a six-axis industrial or articulated-arm robot, as shown in a simplified form in FIG. 2, the angiographic system can also have a normal ceiling or floor-mounted holder for the C-arm 2.

Instead of the C-arm 2 shown by way of example, the angiographic x-ray system can also have separate ceiling and/or floor-mounted supports for the x-ray emitter 3 and the x-ray image detector 4, which for example are electronically rigidly coupled.

These types of angiography system are used in the field of fluoroscopy-controlled interventional repair of abdominal aortic aneurysms.

An abdominal aortic aneurysm (AAA) is a vascular aneurysm on the abdominal aorta. This is treated by insertion of a stent graft. Guidewires and catheters are introduced into the aorta via both groins, via which one or more stent grafts i.e. plastic vessels, are introduced (see FIG. 3), as are shown for example in Cardiology today, January 2011, page 36, under "Product Guide: Guidewires". The aim when introducing this stent graft is to place the "landing zone" of the vascular protheses as far as possible into the healthy vascular wall area, but in doing so not to cover over any important vascular branches. In particular to keep the branches of the liver arteries, the superior mesentenic artery (Arteria Mesenterica Superior), the truncus c(o)eliacus, and the internal pelvic arteries (*A. iliaca* interna) free. A sensible point is the placement of the "main stent" in the aorta in which the said vascular branches may not be closed off. With complex stents, which also include the leg arteries, the final stent must sometimes be assembled from "part stents". For example a stent graft for the leg arteries is "flanged onto" an aorta stent graft, as is described below.

For this "flanging process" a guidewire is first introduced through an opening in the main stent. The part stent is then inserted via this and subsequently deployed, so that it is anchored tightly in the opening of the main stent. Above all the navigation of the guidewire into the narrow opening of the main stent can be problematic, since the two openings are not always aligned in parallel to the observer. Usually they are twisted around the aorta axis so that the opening to be hit is also located behind or in front of the other opening as seen by the observer.

What is desirable here is an angulation of the angiography system which accordingly freely projects the opening.

Previously the wire has been navigated using the standard angulations, for example a perpendicular a-p projection. In some cases better angulations have been found by users by "trial and error".

SUMMARY OF INVENTION

The underlying object of the invention is to embody an angiography system for angiographic examination of an organ, vascular system or other regions of the body of a patient as the object under examination and angiographic examination methods for examining the patient. The object under examination contains two details which hide one another in the x-ray images depending on the angulation of the C-arm. An angulation can automatically be selected in advance which makes individual important details easier to see.

In accordance with the invention the object is achieved for an angiography system and for an angiographic examination method by the features specified in the independent claims. Advantageous embodiments are specified in the dependent patent claims.

The angiography system has an x-ray emitter, an x-ray image detector for creating x-ray images which are attached to the ends of a C-arm, a patient support table with a table plate for supporting the patient, a system control unit, an image system and a monitor.

In accordance with the invention the object is achieved for an angiography system by a facility being provided in the system control unit which is embodied such that,

- it records a 3D dataset of the object under examination registered to the C-arm and records information about the course of the object under examination,
- from this data it calculates a desired and/or optimum angulation of the C-arm and
- it transfers the calculated angulation to the system control unit for setting the C-arm to this angulation.

This results in the user being provided in a simple manner with an automatically pre-selectable angulation, which makes it easier to see important details in the x-ray image since they are not hidden by other details for example.

Inventively the facility calculates the optimum angulation of the C-arm such that the details in the x-ray images do not hide one another.

In an advantageous manner the facility can calculate the optimum angulation of the C-arm such that,
- the projection lies at right angles to the connecting axis of the two details and also
- lies at right angles to the main axis of the object under examination.

Inventively the facility can record the following as information about the course of the object under examination
- the position of the main axis of the object under examination in 3D and
- a fixed point on the object under examination outside the main axis, preferably the position of the more important details, in 3D.

It has proved advantageous for the 3D dataset of the object under examination to be a pre-operative CT, MR angiography registered to the C-arm or an intra-operative rotation angiography to show soft tissue.

In accordance with the invention the information about the course of the object under examination can be determined by defining the center line of the object under examination by a segmentation of the 3D dataset.

In an advantageous manner the object under examination can be a stent in an aorta, wherein the details can be openings of the stent.

Inventively the facility can have a control element by means of which the calculated angulation is able to be transferred to the system control unit for the C-arm.

The object is achieved for an angiographic examination method by the following steps:
S1) Recording a 3D dataset of the object under examination registered to the C-arm,
S2) Determining the course of the object under examination which has a main axis,
S3) Selecting a point on the object under examination outside the main axis,
S4) Selecting two points at a distance from each other on the main axis of the object under examination,
S5) Determining a plane in space formed by the points,
S6) Calculating the perpendiculars to the plane as angulation of the C-arm,
S7) Transferring the calculated angulation for the to the system control unit and
S8) Setting the angulation of the C-arm via the system control unit.

Inventively the object under examination can be a stent in an aorta.

It has proved advantageous for the angulation calculated in accordance with step S6) to be transferred to the C-arm automatically or at the touch of a button.

Inventively the point to be selected on a main stent outside the main axis in accordance with step S3) can be the position of the stent opening in space.

In an advantageous manner the angulation of the C-arm sought can lie both at right angles to the main axis and also at right angles to the connecting axis between two openings of the object under examination.

BRIEF DESCRIPTION OF THE DRAWINGS

The invention is explained in greater detail below with reference to exemplary embodiments shown in the drawing, in which.

DETAILED DESCRIPTION OF INVENTION

Figure 1:
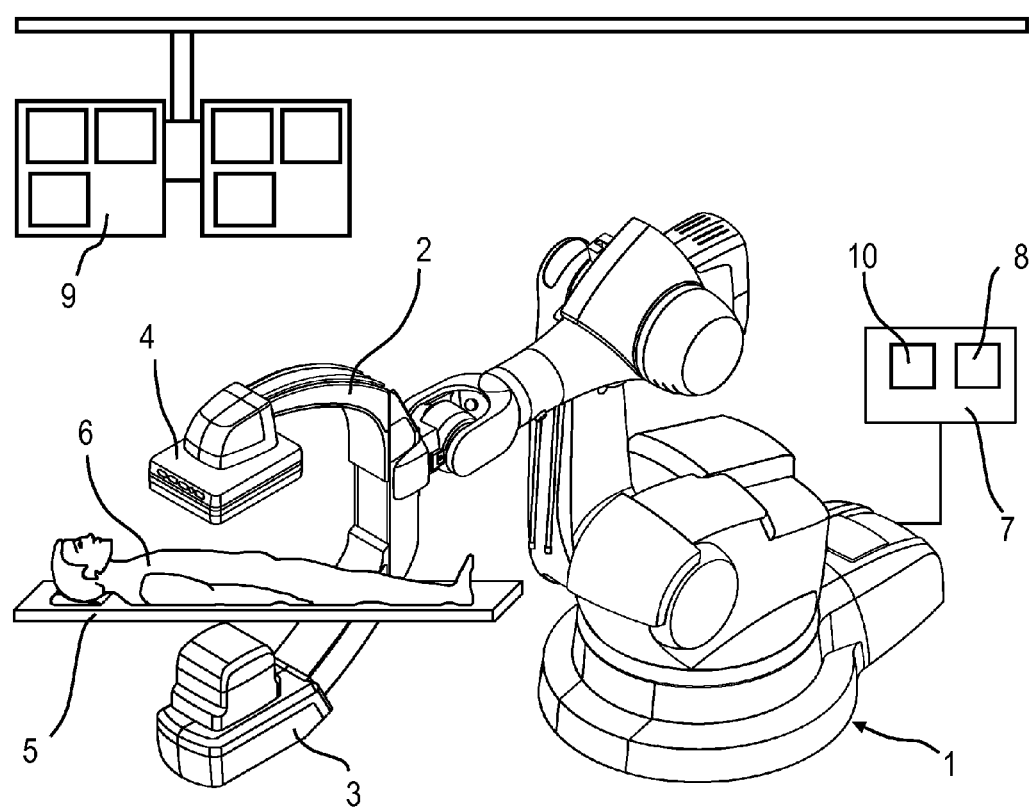
FIG. 1 Shows a known C-arm angiography system with an industrial robot as a support, FIG. 2 Shows an abdominal aorta with an aortic aneurysm, FIG. 3 Shows the aorta in accordance with FIG. 2 with a stent graft inserted, FIG. 4 Shows a diagram to explain the "flanging on" of a part stents to the main stent, FIG. 5 Shows a simplified diagram of the main stent from an optimum viewpoint for navigation, FIG. 6 Shows a view of the main stent in accordance with FIG. 5, FIG. 7 Shows a further view of the main stent in accordance with FIG. 5, FIG. 8 Shows an explanation for calculating the desired view of the opening to be navigated and FIG. 9 Shows details for plane A, B, C according to FIG. 8.
Figure 2:
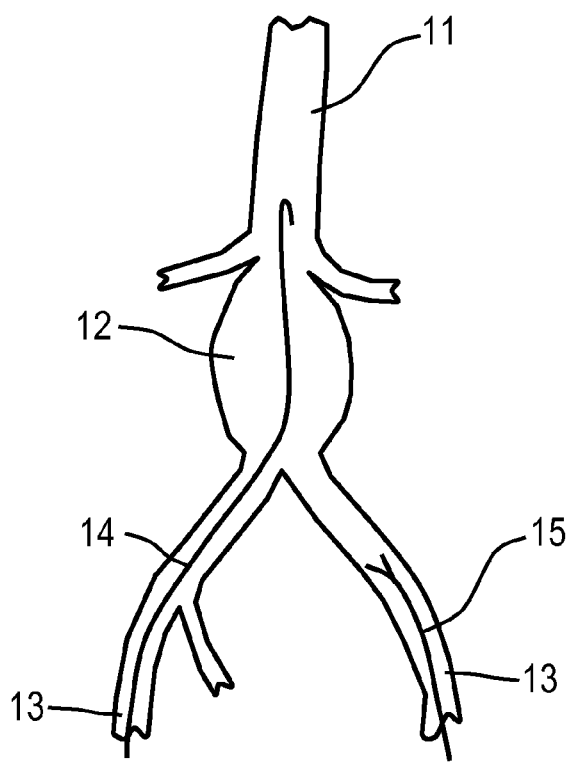

Shown in FIG. 2 is an abdominal aorta 11 having an abdominal aortic aneurysm (AAA) 12. An abdominal aortic aneurysm (AAA) 12 is an aneurysm on the abdominal aorta 11.

Figure 3:
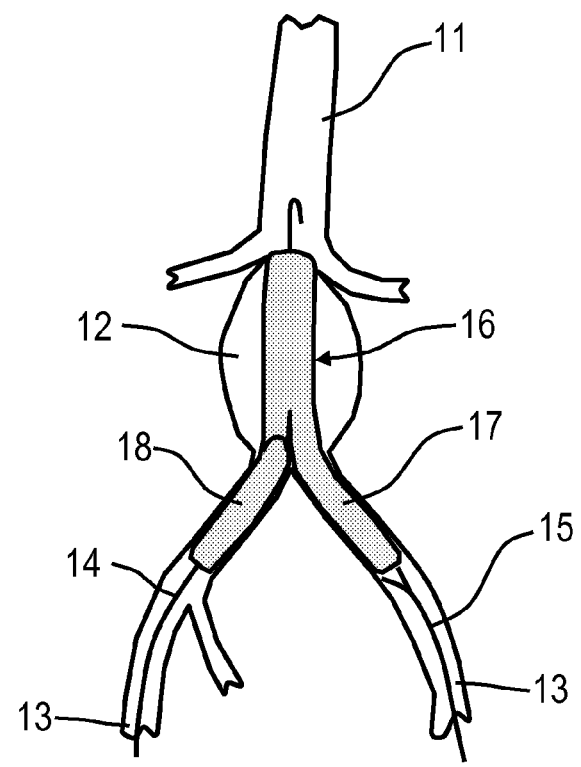

The aortic aneurysm 12 is treated by insertion of a stent graft, i.e. a plastic vessel, as is shown in FIG. 3. To do this, guidewires 14 and catheters 15 are introduced into the aorta via the two groins through the leg arteries 13, via which the stent grafts 16 are introduced.

With complex stent grafts 16, which also include the leg arteries 13, the final stent must sometimes be assembled from "part stents", wherein for example at an aorta stent as main stent 17, which extends through the AAA into one of the leg arteries 13, a part stent 18 for the other leg artery 13 is "flanged on" through what is referred to as a window.

Figure 4:
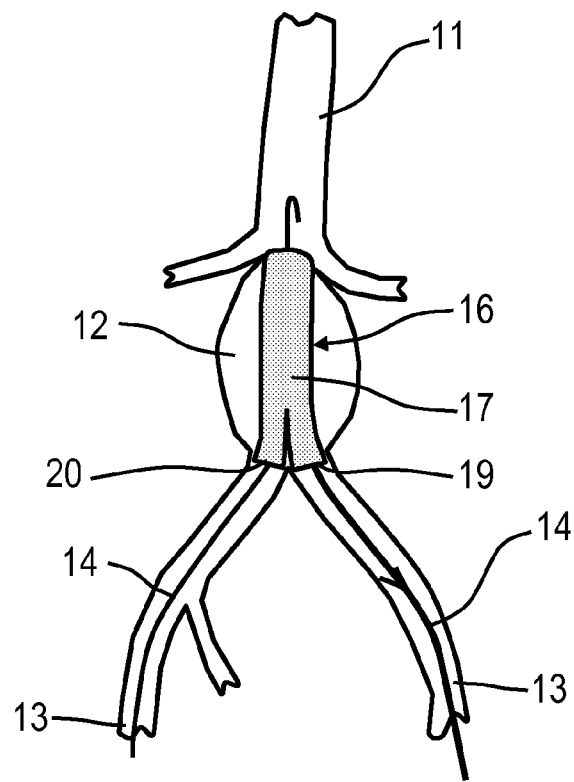

After the main stent 17 has been introduced, as is shown in FIG. 4, a guidewire 14 is introduced through a stent opening 19 in the main stent 17. The part stent 18 (not shown in this figure) is then inserted via said wire, so that it can be anchored in this stent opening 19.

Above all the navigation of the guidewire 14 into the narrow stent opening 19 of the main stent 17 can be problematic if the stent opening 19 and a further opening 20 of the main stent 17 are not always aligned in parallel to the observer in the manner shown in FIG. 4. Usually they are twisted around the aorta axis so that the relevant stent opening 19 for example is also located behind or in front of the other opening 20 from the observer's viewpoint.

Figure 5:
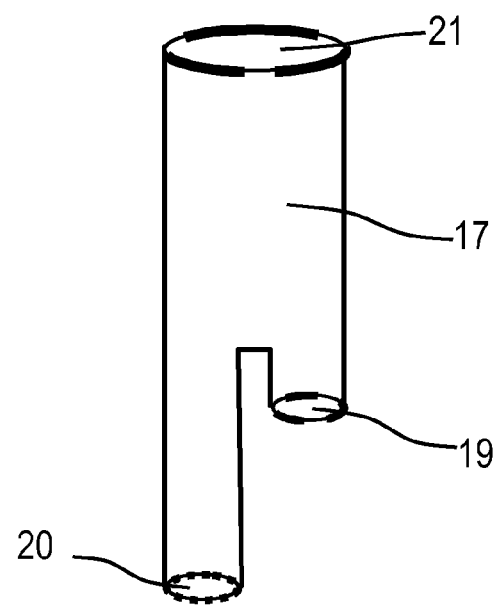

An angulation of the C-arm 2 which "freely projects" the stent opening 19 if possible would now be desirable for navigation, i.e. which allows a "view" of the main stent similar to that depicted in FIG. 5.

Figure 6:
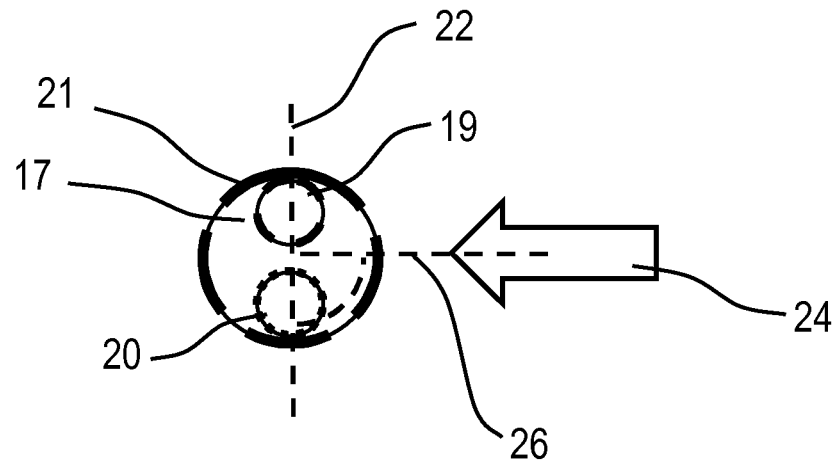
Figure 7:
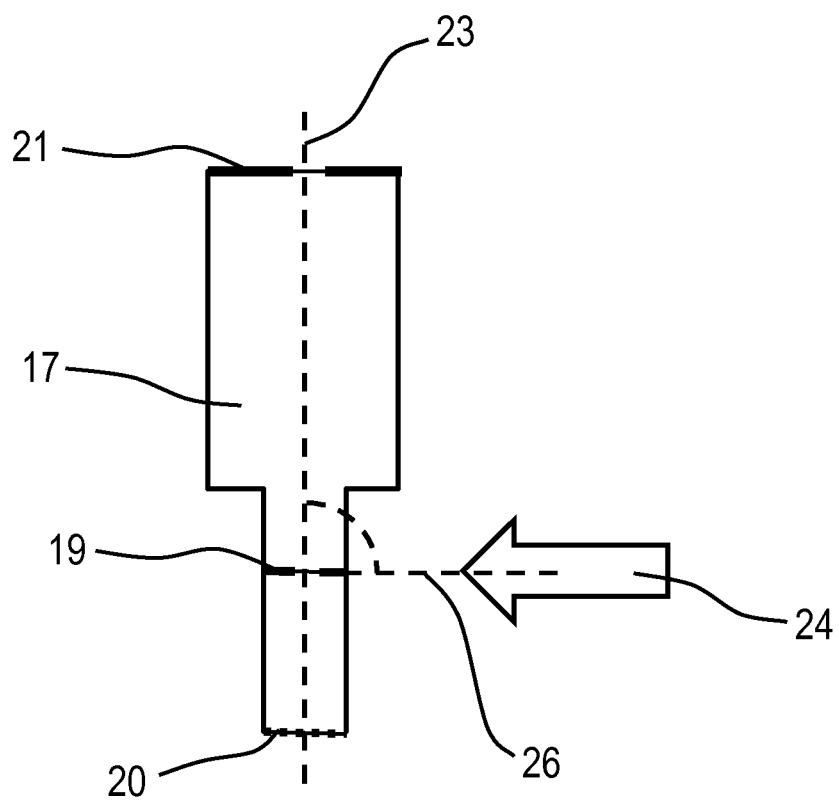

In principle this would be achieved by an angulation which, as shown in FIGS. 6 and 7, simultaneously
- lies at right angles to a connecting axis 22 of the two openings 19 and 20, as is shown in FIG. 6, and also
- lies at right angles to the main axis 23 of the main stent 17, as is shown in FIG. 7, to avoid projectional shortening effects. The view of the observer and thereby the alignment of the C-arm 2 are indicated by the arrows 24.

Making the justified assumption that, with a main stent 17 anchored in the aorta 11, the center line of the aorta 11 is identical to the main axis 23 of the main stent 17, the following information is sufficient for calculation of the optimum angulation for the desired view of the opening to be navigated in:

1. The center line of the aorta 11 in 3D (i.e. the main axis 23 of the main stent 17) and
2. The position of the opening 19 to be hit in 3D.

While the center line of the aorta 11 is known via the segmentation of the pre-operative CT 3D dataset, the position of the opening 19 to be hit is determined via back projection from two 2D images.

Figure 8:
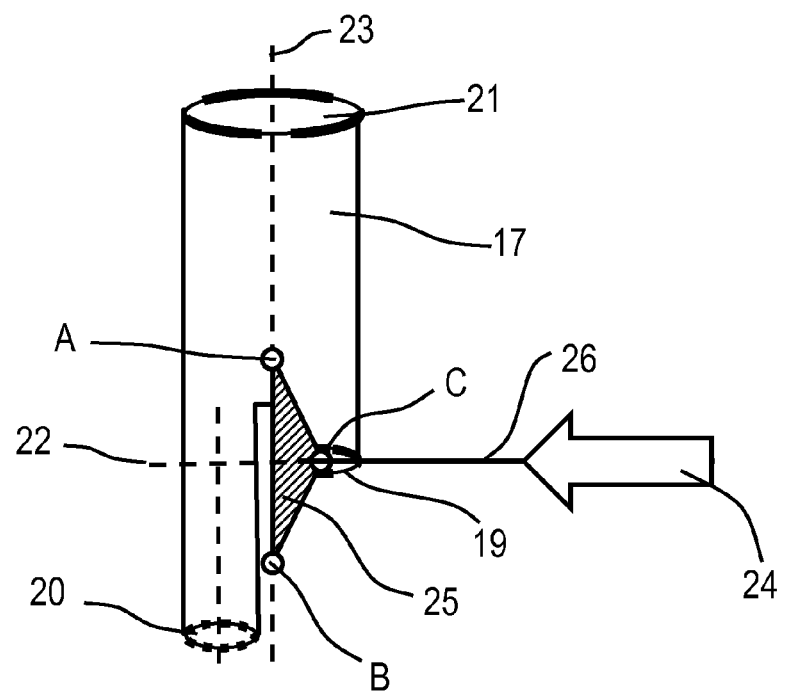
Figure 9:
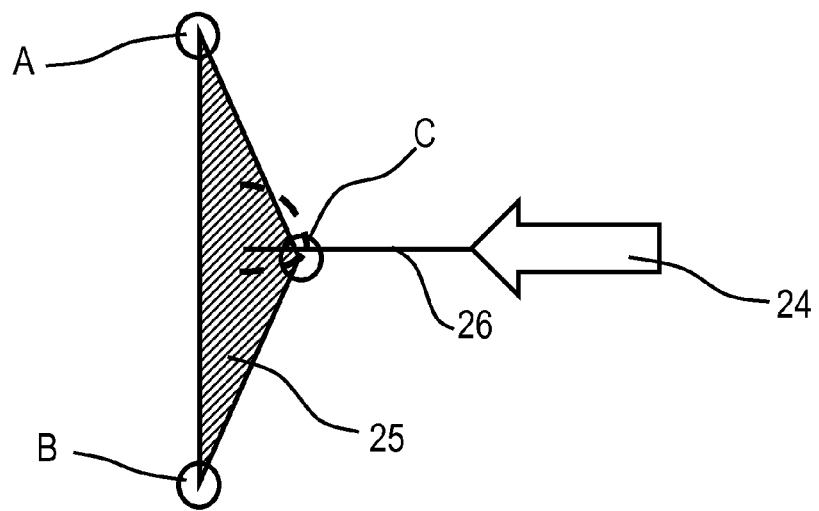

The calculation of the desired view of the opening 19 to be navigated is now explained in greater detail with reference to FIGS. 8 and 9. A prerequisite for the calculation is that the main axis 23 of the main stent 17 and also the position of the opening 19 to be navigated with a center point C are known.

If two points A and B are then selected at a sensible distance on the main axis 23, the points A, B and C then span a plane 25 in space. The angulation sought is now simply the perpendicular to this plane 25 formed by the points A, B and C.

A facility 10 is also provided in the system control unit 7 to calculate the desired view of the stent opening 19 to be navigated, which calculates an angulation of the C-arm 2 from information obtained from the 3D data record, at which the opening 19 to be navigated is typically shown in the aorta or main stent 17 in the x-ray image disrupted as little as possible by other details, such as the second opening 20. To this end two points A and B and also a fixed point on the main stent 17 outside the main axis 23, preferably the position of the stent opening 19 to be hit, are determined on the longitudinal axis of the aorta or main stent 17. On this plane formed by the points A, B and C the perpendiculars 26 are determined and the deviation of the perpendiculars 26 from the position of the x-ray system 1 to 4 are determined. On the basis of this deviation, the correction signal is then calculated, which is converted by the system control unit 7 into a control signal delivered to the x-ray system 1 to 4. This control signal can be triggered automatically. However the C-arm 2 can also only be moved into the optimum angulation once a control element has been actuated by the user.

Inventive prerequisites are thus a 3D dataset of the aorta 11 registered to the C-arm 2 and the information about the course of the aorta 11, for example its center line in this 3D dataset.

The 3D dataset can for example be
- a preoperative CT or MR angiography registered to the C-arm or
- an intra-operative rotation angiography for showing soft tissue with a C-arm system 2 to 4, referred to as a DynaCT, as is described for example in U.S. Pat. No. 7,734,009 B2.

The center line is obtained in the known way via a segmentation of the 3D dataset.

With the aid of this information an angulation of the C-arm 2 is now to be calculated, which allows as "free" a view as possible of the opening 19 to be navigated in the aorta stent or main stent 17.

This "free" view of the stent opening 19 to be navigated has already been explained with reference to FIGS. 5 to 7. What is being sought is an angulation or projection of the C-arm 2, which
- lies at right angles to the connecting axis 22 of the two stent openings 19 and 20 (see perpendiculars 26 in FIG. 6), so that the two stent openings 19 and 20 do not cover or hide each other, and also at the same time
- lies at right angles to the main axis 23 of the main stent 17 (see perpendiculars 26 in FIG. 7), in order to avoid projective shortening effects.

To calculate the corresponding angulation of the C-arm 2 the following information is sufficient (FIG. 8):
- the location of the main axis 23 (H)—i.e. longitudinal axis—of the aorta stent or main stent 17 in 3D and
- a fixed point on the main stent 17 outside the main axis 23, preferably the position in 3D of the stent opening 19 to be hit.

As is explained with reference to FIGS. 8 and 9, the desired angulation of the C-arm 2 can be calculated from this information:

If two points A and B at a sensible distance (for example ~||H—C||) on the main axis 23 of the main stent 17 are selected, the points A, B and C span a plane 25 in space.

The "direction of view" sought, i.e. the angulation of the C-arm 2, is now simply the perpendiculars 26 onto the plane 25, since this
- lies both at right angles the main axis 23,
- and also lies at right angles to the connecting axis 22 between the two openings 19 and 20 (assuming that the main axis 23 of the main stent 17 lies exactly "between" the two openings 19 and 20).

The procedure to obtain the location of the main axis 23 of the main stent 17 and of the center point C is as follows:
- since the main stent 17 has already been placed in the aorta 11, the main axis 23 simply corresponds to the center line of the aorta 11. This is known from the segmentation.
- The center point C can be obtained simply using triangulation:
  - the user records two 2D images of the main stent 17 at different angulations of the C-arm 2 (for example a-p-projection (anterior-posterior) and RAO angle (right anterior oblique) of 30°).
  - In both x-ray images the stent opening 19 is either detected automatically or marked by the user. The 3D position of the center point C can be determined via back projection of the two 2D x-ray images.
- Since the location of the main axis 23 and that of the center point C are now known, the system can automatically determine or define two points A and B on the main axis 23 in a simple manner and
- calculate the angulation of the C-arm 2 at right angles to the plane 25.

The single user interaction is thus the acquisition of the two x-ray images and possibly the marking of the stent opening 19 in the x-ray images. The optimum and/or the desired angulation is then calculated automatically.

There is also the option of the proposed angulation calculated by the facility 10 being able to be transferred automatically or at the press of a button to the C-arm 2.

The location of the plane 25 in principle describes the position and location of the main stent 17 in 3D. If other angulations are viewed as "optimum" for the solution of the problem or of another problem, for example a view which brings the two stent openings 19 and 20 behind one another, this can also be calculated accordingly.

Instead of determining the position of the stent opening 19 to be navigated, any other given fixed point on the main stent 17 outside the main axis 23 can also be selected of which the location in relation to the main axis 23 is known, for example the corresponding other opening 19 of the stent or a marker with a known position.

The invention claimed is:

1. An angiography system for examining an object of a patient, comprising:
    a patient support table for supporting the patient;
    a C-arm;
    an x-ray emitter disposed at an end of the C-arm;
    an x-ray image detector disposed at another end of the C-arm for recording an x-ray image of the object, wherein the object comprises details hiding each other in the x-ray image depending on an angulation of the C-arm;
    a monitor that displays the x-ray image; and
    a control unit configured to:
        record a 3D dataset of the object registered to the C-arm,
        detect a course of the object from the 3D dataset,
        calculate an optimum angulation of the C-arm from the course of the object detected from the 3D dataset, and
        adjust the C-arm to the optimum angulation for recording the x-ray image,
    wherein the optimum angulation of the C-arm lies at a right angle to a connecting axis of the details and lies at a right angle to a main axis of the object.

2. The angiography system as claimed in claim 1, wherein the details in the x-ray images do not hide each other at the optimum angulation of the C-arm.

3. The angiography system as claimed in claim 1, wherein the control unit records a location of a main axis of the object and a fixed point on the object outside the main axis in the 3D dataset for detecting the course of the object.

4. The angiography system as claimed in claim 1, wherein the 3D dataset of the object comprises a pre-operative CT, MR angiography registered to the C-arm or an intra-operative rotation angiography showing soft tissue of the object.

5. The angiography system as claimed in claim 1, wherein the course of the object is determined by defining a center line of the object by a segmentation of the 3D dataset.

6. The angiography system as claimed in claim 1, wherein the object is a stent in an aorta.

7. The angiography system as claimed in claim 6, wherein the details are openings of the stent.

8. An angiographic examination method for examining an object of a patient by an angiography system, comprising:
    recording a 3D dataset of the object registered to a C-arm of the angiography system by an imaging recording method;
    determining a course of the object comprising a main axis by a control unit of the angiography system;
    selecting a point on the object outside the main axis by the control unit;
    selecting two other points at a distance from each other on the main axis of the object;
    determining a plane in space formed by the point and the two other points;
    calculating a perpendicular to the plane as an angulation of the C-arm by the control unit;
    setting the C-arm to the calculated angulation by the control unit; and
    recording an x-ray image of the object at the calculated angulation by the angiography system.

9. The angiographic examination method as claimed in claim 8, wherein the object is a stent in an aorta.

10. The angiographic examination method as claimed in claim 8, wherein the C-arm is set at the calculated angulation automatically or by pressing a button.

11. The angiographic examination method as claimed in claim 8, wherein the point selected on the object outside the main axis is a position of an opening of the object in space.

12. The angiographic examination method as claimed in claim 8, wherein the calculated angulation of the C-arm lies at a right angle to the main axis and lies at a right angle to a connecting axis between two openings of the object.

13. The angiographic examination method as claimed in claim 8, wherein the 3D dataset of the object is recorded by a pre-operative CT, MR angiography registered to the C-arm or an intra-operative rotation angiography showing soft tissue of the object.

* * * * *